(12) United States Patent
Ochiai et al.

(10) Patent No.: US 8,980,316 B2
(45) Date of Patent: Mar. 17, 2015

(54) STABLE TABLET CONTAINING DROXIDOPA

(75) Inventors: Yasushi Ochiai, Ibaraki (JP); Teruko Ariyama, Ibaraki (JP); Hirohisa Kobayashi, Ibaraki (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 361 days.

(21) Appl. No.: 11/914,693

(22) PCT Filed: May 17, 2006

(86) PCT No.: PCT/JP2006/309801
§ 371 (c)(1),
(2), (4) Date: Nov. 16, 2007

(87) PCT Pub. No.: WO2006/123678
PCT Pub. Date: Nov. 23, 2006

(65) Prior Publication Data
US 2009/0074861 A1  Mar. 19, 2009

(30) Foreign Application Priority Data

May 18, 2005  (JP) ................................. 2005-145831

(51) Int. Cl.
*A61K 9/20* (2006.01)
*A61K 31/198* (2006.01)

(52) U.S. Cl.
CPC .............. *A61K 9/2059* (2013.01); *A61K 9/2027* (2013.01); *A61K 31/198* (2013.01)
USPC ...................................................... 424/465

(58) Field of Classification Search
CPC ..... A61K 9/20; A61K 31/198; A61K 9/2027; A61K 9/2059
USPC ...................................................... 424/465
See application file for complete search history.

(56) References Cited

U.S. PATENT DOCUMENTS

| | | | |
|---|---|---|---|
| 3,920,728 A | 11/1975 | Hegedus et al. | |
| 6,287,596 B1 | 9/2001 | Murakami et al. | |
| 6,339,104 B1 | 1/2002 | Nishiguchi et al. | |
| 2002/0177593 A1* | 11/2002 | Ishihara et al. | 514/227.5 |
| 2003/0026835 A1 | 2/2003 | Nishii et al. | |
| 2003/0086967 A1 | 5/2003 | Morita et al. | |
| 2003/0129226 A1 | 7/2003 | Liu et al. | |
| 2004/0028741 A1 | 2/2004 | Fujihara | |
| 2007/0048363 A1 | 3/2007 | Salama | |
| 2008/0095838 A1 | 4/2008 | Chacra-Vernet | |
| 2009/0074861 A1 | 3/2009 | Ochiai et al. | |
| 2009/0143404 A1 | 6/2009 | Fujihara | |
| 2011/0105615 A1 | 5/2011 | Fukushima et al. | |

FOREIGN PATENT DOCUMENTS

| | | | |
|---|---|---|---|
| CA | 2 360 102 A1 * | 8/2000 | ............ A61K 47/36 |
| EP | 0 887 078 A1 | 12/1998 | |
| EP | 2 050 448 A1 | 4/2009 | |
| JP | 50-49252 A | 5/1975 | |
| JP | 52-125630 A | 10/1977 | |
| JP | 08-059490 A | 3/1996 | |
| JP | 2002-506811 A | 3/2002 | |
| JP | 2002-363067 A | 12/2002 | |
| JP | 2003-095928 A | 4/2003 | |
| JP | 2005-533802 A | 11/2005 | |
| JP | 2007-508331 A | 4/2007 | |
| WO | WO 00/47233 A1 | 8/2000 | |
| WO | WO 01/64190 A1 | 9/2001 | |
| WO | WO 01/76565 A1 | 10/2001 | |
| WO | WO 02/24166 A1 | 3/2002 | |
| WO | WO 2004/100929 A1 | 11/2004 | |
| WO | WO 2006/123678 A1 | 11/2006 | |
| WO | WO 2006/126681 A1 | 11/2006 | |
| WO | WO 2006/128022 A2 | 11/2006 | |
| WO | WO 2008/018371 A1 | 2/2008 | |

OTHER PUBLICATIONS

Takagi et al., European Neuropsychopharmacology, 6(1): 43-47 (Jan. 1, 1996).
Chinese Patent Office, First Office Action in Chinese Patent Application No. 200980131311.9 (Mar. 14, 2012).
Chinese State Intellectual Property Office, First Office Action in Chinese Patent Application No. 200680017202.0 (Sep. 25, 2009).
Chinese State Intellectual Property Office, Second Office Action in Chinese Patent Application No. 200680017202.0 (Dec. 9, 2010).
European Patent Office, Extended European Search Report in European Patent Application No. 06746504.7 (May 13, 2009).
European Patent Office, Office Action in European Patent Application No. 06746504.7 (Aug. 3, 2009).
Japanese Patent Office, International Search Report in International Patent Application No. PCT/JP2006/309801 (Jun. 27, 2006).
Japanese Patent Office, International Search Report in International Patent Application No. PCT/JP2009/060584 (Sep. 8, 2009).
Japanese Patent Office, Notice of Reasons for Refusal in Japanese Patent Application No. 2007/516308 (Mar. 21, 2012).
Japanese Patent Office, Notice of Reasons for Refusal in Japanese Patent Application No. 2009/130801 (Mar. 21, 2012).

* cited by examiner

*Primary Examiner* — Aradhana Sasan
(74) *Attorney, Agent, or Firm* — Leydig, Voit & Mayer, Ltd.

(57) ABSTRACT

A tablet containing droxidopa as an active ingredient in a proportion of 20-80 wt % relative to the total weight of the tablet, and characteristically containing at least one excipient selected from mannitol, lactose, erythritol, glucose, sucrose, crystalline cellulose, and corn-derived starch is provided. In addition, a preparation containing corn-derived processed starch or polyvinyl alcohol as a binder and the like, which is a stable tablet containing droxidopa as an active ingredient, is provided.

29 Claims, No Drawings

STABLE TABLET CONTAINING DROXIDOPA

TECHNICAL FIELD

The present invention relates to a tablet droxidopa, which is superior in the preservation stability and easy administrability.

BACKGROUND ART

Droxidopa is a pharmaceutical agent mainly used for improving frozen gait and orthostatic dizziness in patients with Parkinson's syndrome, as well as for treating orthostatic hypotension in dialysis patients. Production of droxidopa tablet has been difficult since it is colored when admixed with various additives such as excipients, binders and the like, and under humidity. As droxidopa preparation, therefore, only dry capsules and fine granules obtained by granulation with an organic solvent without using water are currently commercially available, and capsules are prescribed for most patients.

According to the results of a survey on a dosage form easy to take for patients (easy administrability search), the dosage form easiest to take is tablet, and many patients are known to feel uncomfortable for capsule because it sticks to the throat and the like. Particularly, in view of the fact that many of the patients affected with Parkinson's syndrome and the like, who take droxidopa, are aged individuals, and the proportion of patients with decreased swallowing ability due to the progression of the disease is high, the development of a tablet with easy administrability, particularly an easy-to-take tablet rapidly disintegrated in the oral cavity, which is promptly disintegrated in the oral cavity and does not cause uncomfortableness, has been desired rather than capsules.

As a tablet containing droxidopa, which is rapid disintegrating in the oral cavity, for example, patent reference 1 discloses a rapid-disintegrating tablet containing polyvinyl alcohol, and recites droxidopa as a usable efficacy component. In addition, patent reference 2 discloses a tablet that is rapidly disintegrated in the oral cavity, which characteristically contains starch as an aqueous excipient (binder), where droxidopa is recited as an efficacy component.

However, actual production of a tablet containing droxidopa has not been known.

patent reference 1: WO01/064190
patent reference 2: WO00/47233
non-patent reference 1: Byoin Yakugaku Vol. 11, No. 3, 284-292 (1985)

DISCLOSURE OF THE INVENTION

Problems to be Solved by the Invention

The problem to be solved by the present invention is provision of a tablet of droxidopade, which is superior in the preservation stability and easy administrability.

Means of Solving the Problems

The present inventors have conducted intensive studies and found that a physicochemically stable droxidopa tablet superior in easy administrability can be obtained using particular excipient and binder and managing the water content, which resulted in the completion of the present invention. In other words, they have succeeded in obtaining a stable droxidopa tablet free of coloring and capable of maintaining the quality for a long time.

Accordingly, the present invention relates to

[1] a tablet comprising droxidopa as an active ingredient and at least one excipient selected from mannitol, lactose, erythritol, glucose, sucrose, crystalline cellulose and corn-derived starch;
[2] the tablet of [1], which is produced by direct tabletting method;
[3] the tablet of [1] or [2], wherein the content of droxidopa is 20-80 wt % relative to the total weight of the tablet;
[4] the tablet of [1], further comprising corn-derived starch and/or polyvinyl alcohol as a binder;
[5] the tablet of [4], wherein the content of droxidopa is 20-80 wt % relative to the total weight of the tablet;
[6] the tablet of [4] or [5], wherein the binder is corn-derived processed starch;
[7] the tablet of [6], wherein the corn-derived processed starch is partially or entirely pregelatinized cornstarch;
[8] the tablet of [7], wherein the partially or entirely pregelatinized cornstarch is comprised in a proportion of 0.3-6% of the total weight;
[9] the tablet of [4] or [5], wherein the binder is polyvinyl alcohol;
[10] the tablet of [9], wherein the polyvinyl alcohol is comprised in a proportion of 0.001-5% of the total weight;
[11] the tablet of any of [1] to [10], wherein the content of the excipient is 15-78 wt %;
[12] the tablet of any of [1] to [11], which is produced via a granulation step using water;
[13] the tablet of any of [1] to [12], which has a water content of 0.6 wt % or below relative to the total weight of the tablet;
[14] the tablet of [1] or [2], which is rapidly disintegrated in the oral cavity and comprises the following (1) and (2), wherein the droxidopa content is 20-80 wt % relative to the total weight of the tablet:
(1) at least one excipient selected from mannitol, erythritol and lactose,
(2) a disintegrant comprising cornstarch or partly pregelatinized corn-derived starch;
[15] the tablet of [14], further comprising corn-derived starch and/or polyvinyl alcohol as a binder;
[16] the tablet of [15], wherein the binder is a partially or entirely pregelatinized cornstarch contained in a proportion of 0.5-3% of the total weight;
[17] the tablet of [15], wherein the binder is polyvinyl alcohol contained in a proportion of 0.001-2% of the total weight;
[18] the tablet of any of [14] to [17], wherein the weight ratio of excipient:total weight of corn-derived starch is 5:5-9.5:0.5;
[19] the tablet of any of [14] to [18], wherein the excipient is mannitol;
[20] the tablet of any of [1] to [19], wherein the droxidopa has an average particle size of 20 μm or above;
[21] a production method of the tablet of any of [1] to [20], comprising the following steps (1)-(3):
(1) a step of granulating a mixture of droxidopa and an additive,
(2) a step of drying a granulated production intermediate to give a granular production intermediate having a water content of 1 wt % or below, and
(3) a step of tabletting the granular production intermediate obtained in the aforementioned (2); and
[22] the method of [21], wherein the droxidopa has an average particle size of 20 μm or above.

Effect of the Invention

According to the present invention, it is now possible to produce a droxidopa tablet free of coloring and capable of maintaining the quality for a long time. The droxidopa tablet according to the present invention does not require any special production facility at all and can be produced with ease in a conventional facility, and has suitable hardness that prevents breakage during a distribution process. Moreover, the tablet of the present invention is easy to handle and has a suitable size for easy administration. Furthermore, the tablet of the present invention can also be processed into an intraoral cavity rapid-disintegrating tablet that rapidly disintegrates in the oral cavity, thereby enabling compliance improvement for the elderly with decreased swallowing ability.

BEST MODE FOR EMBODYING THE INVENTION

The mannitol, lactose, erythritol, glucose, sucrose (purified sucrose) and crystalline cellulose to be used in the present invention are not particularly limited, and those described in "the Japanese Pharmacopoeia" or "Japanese Pharmaceutical Excipients", which are generally used by those of ordinary skill in the art, can be used. For production by directly tabletting method, those specially improved for use for direct tabletting are preferably used.

While the average particle size of these excipients is not particularly limited, it is preferably 10-500 µm, more preferably 20-200 µm, still more preferably 20-100 µm. The measurement method of the particle size is, for example, a method including use of a laser diffraction and scattering particle size distribution measurement apparatus for the measurement of a particle size of a micrometer order, or a method including use of a dynamic light scattering particle size distribution measurement apparatus for the measurement of a particle size of a nanometer order.

Where necessary, a pulverized product is used as appropriate to achieve a desired particle size. The pulverization method is, for example, a method including use of a stream pulverizer or a hammer pulverizer.

Polyvinyl alcohol (PVA) is, for example, a polymer obtained by saponifying polyvinyl acetate, and is not particularly limited as long as it is acceptable for use as a pharmaceutical product. Preferably, one with a saponification degree of 78-96 mol % can be used. In addition, 4 wt % aqueous solution of polyvinyl alcohol has a viscosity as measured by a Hoeppler viscometer at 20° C. of 1-50 mPa·s, more preferably 2-40 mPa·s, still more preferably 3-30 mPa·s, further preferably 4-20 mPa·s, particularly preferably 4.5-6 m Pa·s.

In the present invention, "cornstarch" is not particularly limited as long as it is generally used as a pharmaceutical product, and includes any natural cornstarch. It is preferably obtained from nonglutinous race, particularly preferably obtained from white corn as a starting material. While the average particle size is not particularly limited, it is preferably not more than 100 µm, more preferably not more than 50 µm.

In the present specification, "corn-derived starch" is a concept including not only the aforementioned "cornstarch" but also "corn-derived processed starch" obtained by a heat treatment, a chemical treatment and the like of the cornstarch. The aforementioned corn-derived processed starch is not particularly limited as long as it can be used as a pharmaceutical product and, for example, cornstarch-derived processed starches such as soluble starch, pregelatinized starch, partly pregelatinized starch, hydroxypropylated starch and the like can be mentioned.

The aforementioned corn-derived processed starch is preferably a starch free of chemical modification, such as introduction of substituent by a chemical reaction and the like. Namely, a processed starch obtained by a heat treatment is preferable. Specifically, pregelatinized starch or partly pregelatinized starch can be used. Here, the proportion of pregelatination of a partially or entirely pregelatinized starch obtained by a heat treatment of cornstarch is not particularly limited.

As the aforementioned pregelatinized starch or partly pregelatinized starch, a commercially available product can also be used. In addition, a viscous liquid starch obtained by dispersing cornstarch in water and heat treating the dispersion to allow partial or entire pregelatination can also be used. In the present specification, such pregelatinized starch or partially pregelatinized starch is hereinafter referred to as "partially or entirely pregelatinized cornstarch". The viscous liquid starch is preferably used as a binding solution for granulation.

A partially or entirely pregelatinized cornstarch in a viscous liquid form can be produced by the following method. That is, a cornstarch wherein partial or entire cornstarch is pregelatinized can be obtained by dispersing cornstarch in water in a proportion of 0.5-10%, and heat treating the dispersion at 60° C.-100° C. for 0.1-15 min. Preferably, a partially or entirely pregelatinized cornstarch obtained by treating at 62-95° C., more preferably 65° C.-85° C., particularly preferably 68-75° C., for preferably 0.5-10 min, more preferably 1-8 min, particularly preferably 2-6 min is used as a binder.

The excipient to be used in the present invention is one acceptable for use as a pharmaceutical product, which does not influence the stability of droxidopa. Specifically, it is at least one selected from mannitol, lactose, erythritol, glucose, sucrose, crystalline cellulose and corn-derived starch or a mixture thereof. That is, using these excipients, a tablet containing droxidopa, which is free of coloring and permits preservation for a long time can be produced.

In the case of a tablet characterized by rapid disintegration in the oral cavity (hereinafter sometimes to be referred to as an intraoral cavity rapid-disintegrating tablet in the present specification), mannitol, erythritol or lactose is particularly preferable from the aspect of disintegration, and mannitol is especially preferable.

In the present invention, being "rapidly disintegrating in the oral cavity" means complete disintegration preferably within 80 seconds, more preferably within 60 seconds, still more preferably within 40 seconds, particularly preferably within 30 seconds, after placing the tablet in the oral cavity, though subject to an interindividual difference to some extent.

The binder to be used in the present invention is one acceptable for use as a pharmaceutical product, which is at least one selected from corn-derived starch and polyvinyl alcohol. That is, using these binders, a tablet containing droxidopa, which is free of coloring and permits preservation for a long time can be produced. The binder is more preferably one derived from cornstarch, more preferably processed starch derived from cornstarch. Of these, a cornstarch free of chemical modification, such as introduction of substituent by a chemical reaction and the like, is preferable, and the aforementioned partially or entirely pregelatinized cornstarch, which is obtained by dispersing cornstarch in water and heating the dispersion, can be particularly preferably used.

The tablet of the present invention is explained in detail in the following.

I. Tablet

The present invention provides a tablet comprising droxidopa as an active ingredient. The tablet characteristically contains at least one excipient selected from mannitol, lactose, erythritol, glucose, sucrose, crystalline cellulose and corn-derived starch, and optionally contains corn-derived starch and/or polyvinyl alcohol as further binder(s).

The tablet of the present invention can be produced via a granulation step or by a direct tabletting method.

The tablet of the present invention is a high dose droxidopa tablet preferably containing droxidopa as an active ingredient in a proportion of 20-80% relative to the total weight of the tablet. Specifically, it contains droxidopa in a proportion of not less than 20 wt %, preferably not less than 40 wt %, more preferably not less than 50 wt %, of the total weight of the tablet.

As preferable binder, corn-derived starches can be mentioned. Of these, a cornstarch free of chemical modification, such as introduction of substituent by a chemical reaction and the like, is more preferable, and the aforementioned partially or entirely pregelatinized cornstarch, which is obtained by dispersing cornstarch in water and heating the dispersion, is particularly preferably used.

That is, the tablet of the present invention is preferably a tablet containing at least one excipient selected from mannitol, lactose, erythritol, glucose, sucrose, crystalline cellulose and corn-derived starch, and partially or entirely pregelatinized cornstarch as a binder.

The tablet of the present invention preferably contains an excipient in a proportion of 15%-78% and a binder in a proportion of generally 1%-6%, both relative to the total weight of the tablet. Specifically, when the binder is cornstarch or a processed starch derived from cornstarch, it is preferably contained in a proportion of 0.3%-6%, more preferably 0.5-5%, and when the binder is polyvinyl alcohol, it is preferably contained in a proportion of 0.001%-5%, more preferably 0.001-4%.

While the tablet of the present invention does not substantially contain a binder other than corn-derived starch or polyvinyl alcohol, this is because a binder other than corn-derived starch or polyvinyl alcohol influences the stability of the tablet containing droxidopa.

Accordingly, the tablet of the present invention does not substantially contain a binder such as polyvinylpyrrolidone, hydroxypropyl methylcellulose, hydroxypropylcellulose, agar, gelatin and the like. However, these binders may be contained in an amount free of an adverse influence on the stability (coloring property) of the tablet.

II. Intraoral Rapid-Disintegrating Tablet

The tablet of the present invention encompasses an intraoral rapid-disintegrating tablet. That is, using cornstarch as a disintegrant, an intraoral rapid-disintegrating tablet containing droxidopa as an active ingredient, which is free of coloring and permits preservation for a long time can be produced.

When the tablet of the present invention containing droxidopa as an active ingredient is an intraoral rapid-disintegrating tablet, it characteristically contains the following (1) and (2):

(1) at least one excipient selected from mannitol, erythritol and lactose,
(2) at least one disintegrant selected from cornstarch and partly pregelatinized corn-derived starch. Furthermore, the intraoral rapid-disintegrating tablet of the present invention may contain corn-derived starch and/or polyvinyl alcohol as a binder.

As an excipient here, mannitol can be preferably used.

As a binder, moreover, corn-derived starch can be preferably mentioned. Still more preferably, it is corn-derived processed starch, and a cornstarch free of chemical modification, such as introduction of substituent by a chemical reaction and the like, is especially preferable, and partially or entirely pregelatinized cornstarch, which is obtained by dispersing cornstarch in water and heating the dispersion, is particularly preferably used.

That is, the intraoral rapid-disintegrating tablet of the present invention is particularly preferably a tablet containing mannitol and partially or entirely pregelatinized cornstarch.

For the intraoral rapid-disintegrating tablet of the present invention to be rapidly disintegrated in the oral cavity, the content ratio of the excipient described in the aforementioned (1) and the total weight of corn-derived starch is preferably 5:5-9.5:0.5, more preferably 6:4-9:1. Here, the "total weight of corn-derived starch" means the total amount of cornstarch or partly pregelatinized starch as a disintegrant and corn-derived starch (encompassing cornstarch and corn-derived processed starch) as a binder.

A binder is contained in a proportion of generally 0.001%-5 wt %. Specifically, when the binder is starch derived from cornstarch, it is preferably contained in a proportion of 0.3%-5 wt %, more preferably 0.5-3 wt %, and when the binder is polyvinyl alcohol, it is preferably contained in a proportion of 0.001%-2%.

While the intraoral rapid-disintegrating tablet of the present invention does not substantially contain a binder other than corn-derived starch or polyvinyl alcohol, this is because a binder generally acts toward the prevention of rapid disintegration in the oral cavity and a binder other than corn-derived starch or polyvinyl alcohol influences the stability of the tablet containing droxidopa. Accordingly, the tablet of the present invention does not substantially contain a binder such as polyvinylpyrrolidone, hydroxypropyl methylcellulose, hydroxypropylcellulose, agar, gelatin and the like. However, these binders may be contained in an amount free of an adverse influence on the disintegration property and stability (coloring property) of the tablet.

The tablet of the present invention, namely, the tablets described in the above-mentioned I and II, may contain where appropriate, besides the described components, an auxiliary component acceptable for use as a pharmaceutical product, such as disintegrant, lubricant, sweetener, acidulant, flavor, dyes, preservative, antioxidant, stabilizer, surfactant and the like, for the purpose of disintegration, molding, or stabilizing, improved taste and the like.

A lubricant is used for producing a tablet in the present invention. The kind and amount thereof are not particularly limited as long as they are within the ranges acceptable for use as a pharmaceutical product. Usable lubricant includes, for example, magnesium stearate, stearic acid, calcium stearate, sodium stearyl fumarate, sucrose fatty acid ester, talc, hydrogenated oil, Carnauba wax and the like. It is desirable to determine a suitable amount within the range uninfluential for the disintegration property of the tablet. Tabletting with a trace amount of lubricant by external lubrication method is effective. A lubricant is added in a proportion of generally about 0.5-3 wt % for the internal lubrication method. According to the external lubrication method, since a smaller amount suffices for showing a lubricant effect, a lubricant is generally added in a proportion of about 0.05-0.5 wt %.

A method of producing a tablet in the present invention is not particularly limited, and a method widely employed by those of ordinary skill in the art can be used. That is, (1) droxidopa, (2) an excipient selected from mannitol, lactose, erythritol, glucose, sucrose, crystalline cellulose and corn-derived starch and, where necessary, an additive such as corn-derived starch and/or polyvinyl alcohol and the like as a binder are mixed. For production of an intraoral rapid-disintegrating tablet, cornstarch or partly pregelatinized corn-derived starch is added as a disintegrant. Further, a lubricant is added, mixed therewith and the mixture is compression molded using a suitable tabletting machine such as a rotary tabletting machine, single tabletting machine, oil hydraulic press machine and the like, whereby tablets can be obtained. It is also possible to perform tabletting without adding a lubricant to the mixture by external lubrication method.

Where necessary, the mixture may be granulated and then compression molded.

Since coloring tendency of droxidopa is accelerated by the presence of water, the water content of the tablet in the present invention is preferably as small as possible.

Specifically, the water content of tablet is preferably not more than 1 wt %, more preferably not more than 0.8 wt %, still more preferably not more than 0.6 wt %, particularly preferably not more than 0.4 wt %.

Accordingly, a production method of the tablet of the present invention, comprising the following steps (1)-(2):
(1) a step of producing a granular production intermediate having a water content of 1.5 wt % or below by granulating a mixture of droxidopa and an additive, and
(2) a step of tabletting the granular production intermediate obtained in the aforementioned (1) is also within the scope of the present invention.

Here, the additive means a component other than droxidopa, such as excipient, disintegrant, binder, lubricant and the like, which is contained in the tablet of the present invention.

To adjust the water content, each of the above-mentioned production steps is preferably performed under dry conditions to the extent possible. When the production includes a granulation step of a granular production intermediate, the water content immediately after granulation is preferably not more than 1.5 wt %, more preferably 1 wt %, still more preferably 0.6 wt %, particularly preferably not more than 0.4 wt %. In addition, it is preferable to immediately dry the production intermediate after granulation sufficiently by a method such as heating blowing air and the like.

As a granulation method, extrusion granulation method, compression granulation method, melt granulation method, spray dry granulation method, fluidized bed granulation method, pulverization granulation method, stirring granulation method and the like can be mentioned.

In addition, the tablet of the present invention is preferably provided with a moisture absorption agent enclosed together, such as silica gel and the like as necessary.

As for droxidopa, a milled product is preferably used. While the average particle size is not particularly limited, it is preferably 20-500 μm, more preferably 20-200 μm, still more preferably 20-100 μm. To improve the easy administrability of the tablet, moreover, the average particle size of droxidopa to be the starting material is particularly preferably 25-50 μm. The particle size distribution of droxidopa is preferably as uniform as possible. Specifically, 90% D is preferably not more than 200 μm, preferably not more than 160 μm. As a milling method, for example, a method using a jet mill or a hammer mill can be mentioned.

The tablet of the present invention has hardness of not less than 30N. According to the present invention, it is possible to produce a droxidopa high content tablet containing not less than 50% of droxidopa, and having a diameter of not more than 15 mm, preferably not more than 12 mm. Specifically, a 9-11 mm tablet can be produced as a preparation containing 200 mg of droxidopa, and an about 7-9 mm tablet can be produced as a preparation containing 100 mg of droxidopa.

The shape of the tablet of the present invention is not particularly limited, and it may be any such as round shape tablet, circular shape R tablet, circular shape flat with bevel edge tablet, capsule shape tablet, various tablets of abnormal shape and the like. The tablet may be a scored tablet.

The present invention is explained in more detail in the following by referring to Examples and Comparative Examples, which are not to be construed as limitative.

EXAMPLES

The following are the starting materials used in the Examples of the present specification.
1. D-mannitol (manufactured by KYOWA HAKKO KOGYO Co., Ltd.)
2. cornstarch trade name: cornstarch (XX16)W (manufactured by NIHON SHOKUHIN KAKO CO., LTD)
3. magnesium stearate (St-Mg) (manufactured by TAIHEI CHEMICAL INDUSTRIAL CO., LTD.)
4. silica gel trade name: Dryern (manufactured by YAMANI YAKUHINI Co., Ltd.)
5. sodium stearyl fumarate trade name: PRUV (manufactured by JRS Pharma LP)
6. lactose trade name: lactose 200M (manufactured by DMV)
7. pregelatinized starch trade name: amycol C (manufactured by NIPPON STARCH CHEMICAL CO., LTD.)
8. xylitol trade name: xylit fine powder (manufactured by Towa Chemical Industry Co., Ltd.)
9. methylcellulose trade name: Metolose SM-25 (manufactured by Shin-Etsu Chemical Co., Ltd.)
10. D-mannitol trade name: PEARLITOL160 (manufactured by ROQUETTE)
11. cornstarch trade name: Nisshoku cornstarch W (manufactured by NIHON SHOKUHIN KAKO CO., LTD)
12. citric anhydride (manufactured by San-Ei Gen F.F.I., Inc.)
13. aspartame (manufactured by Ajinomoto Co., Inc.)
14. erythritol (manufactured by NIKKEN CHEMICAL Co., Ltd.)
15. glucose (Nacalai Tesque reagent)
16. sucrose (Nacalai Tesque reagent)
17. microcrystalline cellulose trade name: AvicelPH-102 (manufactured by Asahi Kasei Corporation)
18. partly pregelatinized starch trade name: PCS-PC-10 (manufactured by Asahi Kasei Corporation)
19. hydroxypropyl starch trade name: HPS-101 (manufactured by Freund Corporation)
20. D-sorbitol (manufactured by Towa Chemical Industry Co., Ltd.)
21. trehalose (manufactured by Asahi Kasei Corporation)
22. maltitol trade name: Amalty MR (manufactured by Towa Chemical Industry Co., Ltd.)
23. fructose (Nacalai Tesque reagent)
24. potato starch (Nacalai Tesque reagent)
25. rice starch trade name: Micro Pearl (manufactured by Shimada Chemical Co.)
26. polyvinyl alcohol trade name: GOHSENOL EG-05 (manufactured by Nippon Synthetic Chemical Industry Co., Ltd.)
27. polyvinyl pyrrolidone trade-name: Plasdone K30 (manufactured by ISP Japan Ltd.)
28. hydroxypropylcellulose trade name: HPC-L (manufactured by Nippon Soda Co., Ltd.)
29. hydroxypropyl methylcellulose trade name: TC-5E (manufactured by Shin-Etsu Chemical Co., Ltd.)

Example 1

Cornstarch (200 g) was dispersed in purified water, and the dispersion was heated up to immediately before boiling to allow gelatinization and cooled to give 1% starch glue (20 kg). A mixture of the above-mentioned components other than magnesium stearate was charged in a fluidized bed granulator (FLF-30, manufactured by Freund Corporation), the above-mentioned 1% starch glue was added and the mixture was granulated. The water content of the granules was 0.3%. After drying, the granules were tableted using external lubrication system (manufactured by KIKUSUI SEISAKUSHO LTD.) with magnesium stearate (St-Mg) to give about 2500 tablets with diameter 10 mm, weight about 400 mg. The obtained tablet was completely disintegrated in 20-30 seconds after being placed in the oral cavity. The composition ratios of respective components are shown in Table 1.

TABLE 1

| preparation 1 | amount charged (kg) |
|---|---|
| L-threo DOPS | 14.5 |
| D-mannitol[1] | 13.05 |
| cornstarch[2] | 1.43 |
| St-Mg[3] | trace amount |

The following shows the evaluation results of the properties of the above-mentioned tablets.

Test Example 1

The stability of the tablet of Example 1 was evaluated. The tablet of Example 1 was placed in a brown glass, which was tightly sealed and preserved at 25° C. and 40° C. for 3 months. Changes in the appearance and droxidopa content are shown (n=3). The color difference was measured using a spectral calorimeter (SE-2000: manufactured by Nippon Denshoku Industries Co., Ltd.), and a difference (ΔE) from tablet specimens (n=5) immediately after tabletting is shown. The changes of appearance are shown in Table 2 below. The appearance judgment criteria are as follows:
−: no change
±: slight change
+: change
++: remarkable change.
In general, the color difference is not more than ΔE=3, which resists visual observation of the changes.

From the results of Table 2, the tablet of preparation 1 was stable even after preservation at 25° C. for 3 months and 40° C. for 1-6 months. Furthermore, while the water content of the tablet can be decreased by enclosing silica gel in a preservation bottle, it has been clarified that coloring can be suppressed and the stability is further improved even after severer preservation at 60° C. for 1 month, by preservation of preparation 1 in the presence of a desiccant (silica gel). That is, the tablet of the present invention is more preferably packed with a desiccant such as silica gel and the like.

Moreover, the droxidopa content tablet of Example 1 was measured.

TABLE 3

| sample | immediately after tabletting | 25° C. × 3 M | 40° C. × 3 M |
|---|---|---|---|
| preparation 1 | 100.0 | 101.7 | 101.9 |
| preparation 1 + silica gel | 100.0 | 102.0 | 99.7 |

From the above-mentioned results, the tablet of Example 1 showed less change in appearance and was stable. Consequently, the droxidopa content of the tablet hardly changed at 25° C. for 3 months and at 40° C. for 3 months, and the preparation was found to be also chemically stable.

Comparative Example 1

The components in the following Table 4 were mixed and, using punch and die coated with magnesium stearate suspended in ethanol and dried, and an oil hydraulic press (manufactured by RIKEN), the mixture was compressed at a pressure of 40 kgf/cm$^2$ to give tablets with diameter 10 mm, weight 400 mg.

TABLE 4

| component | amount (mg) per tablet |
|---|---|
| L-threo DOPS | 200 |
| xylitol[8] | 180 |
| methylcellulose[9] | 20 |
| magnesium stearate[3] | trace amount |

TABLE 2

| sample | evaluation | initial value | 60° C. × 1 M | 40° C. × 1 M | 40° C. × 3 M | 40° C. × 6 M | 25° C. × 3 M |
|---|---|---|---|---|---|---|---|
| preparation 1 | appearance judgment | − | + | ± | ± | ± | − |
| | color tone | white | pale-brown | pale-brown | pale-brown | pale-brown | white |
| | color difference (ΔE) | 0.00 | 6.51 | 1.02 | 1.70 | 2.09 | 0.6 |
| | water content (%) | n.d. | 0.64 | n.d. | 0.55 | n.d. | 0.48 |
| preparation 1 + silica gel | appearance judgment | − | ± | − | − | − | − |
| | color tone | white | pale-brown | white | white | white | white |
| | color difference (ΔE) | 0.00 | 2.37 | 0.41 | 0.78 | 0.80 | 0.26 |
| | water content (%) | n.d. | 0.39 | n.d. | 0.27 | n.d. | 0.27 | n.d.: no data

The tablet having the above-mentioned formulation was tightly sealed in a brown glass bottle, and preserved in a tightly sealed container at 40° C. The results are as shown in Table 5.

TABLE 5

| sample | evaluation | initial value | 40° C. × 1 M |
|---|---|---|---|
| preparation 1 | appearance judgment | – | ± |
|  | color tone | white | pale-brown |
| Comparative Example | appearance judgment | – | ++ |
|  | color tone | white | partially blackened |

The preparation of Comparative Example 1 containing xylitol and methylcellulose developed visually-observable black spots on the tablet after lapse of 1 month, and the stability was very poor.

Example 2

Cornstarch (7 g) was dispersed in purified water, gelatinized and cooled to give 1% starch glue (700 g). A mixture of the above-mentioned components other than sodium stearyl fumarate (PRUV) was charged in a spray granulator (RABO-1, manufactured by POWREX CORPORATION), and was granulated using the above-mentioned 1% starch glue. After drying, sodium stearyl fumarate was added to the granules and the mixture was tableted using a rotary tableting machine to give about 1000 tablets with diameter 10 mm, weight about 400 mg. The obtained tablet was completely disintegrated in 20-30 seconds after being placed in the oral cavity. The composition ratios of respective components are shown in Table 6.

TABLE 6

| preparation 2 | amount charged (g) |
|---|---|
| L-threo DOPS | 600 |
| D-mannitol[1] | 540 |
| cornstarch[2] | 60 |
| PRUV[5] | 36 |

L-threo DOPS is droxidopa, and
PRUV[5] is sodium stearyl fumarate.

Example 3

The components in the following Table 7 were mixed and, using punch and die coated with magnesium stearate suspended in ethanol and dried, and an oil hydraulic press (manufactured by RIKEN), the mixture was compressed at a pressure of 20 kgf/cm² to give tablets with diameter 9 mm, weight 300 mg, hardness about 3 kg, disintegration time in the oral cavity 20-30 seconds.

TABLE 7

| preparation 3 | amount (mg) per tablet |
|---|---|
| L-threo DOPS | 200 |
| lactose[6] | 90 |
| pregelatinized starch[7] | 10 |
| St-Mg[3] | trace amount |

Example 4

Droxidopa and the following excipients were mixed at 1:1 in a mortar and the mixture was compressed at a pressure of 20 kgf/cm² using an oil hydraulic press (manufactured by RIKEN). The obtained tablets were preserved under the respective conditions of 60° C. (heated) or 40° C./75% RH (humidified) for 2 weeks. The 60° C. 2 week preservation product was measured for the color difference from the initial stage preservation product using a spectral calorimeter (SE-2000: manufactured by Nippon Denshoku Industries Co., Ltd.). A product showing a color difference of ΔE=less than 4 was further preserved at 40° C./75% RH for 2 weeks and the presence or absence of deliquescence was confirmed.

TABLE 8

| No. | additive | 60° C. × 2 W color difference | 40° C. 75% × 2 W deliquescence |
|---|---|---|---|
| 1 | D-mannitol[1] | 0.72 | none |
| 2 | lactose[6] | 1.74 | none |
| 3 | erythritol[14] | 2.65 | none |
| 4 | glucose[15] | 2.39 | none |
| 5 | sucrose[16] | 1.30 | none |
| 6 | crystalline cellulose[17] | 3.81 | none |
| 7 | pregelatinized starch (corn-derived)[7] | 3.47 | none |
| 8 | partly pregelatinized starch (corn-derived)[18] | 3.50 | none |
| 9 | cornstarch[2] | 2.83 | none |
| 10 | hydroxypropyl starch[19] | 7.12 | n.d. |
| 11 | xylitol[8] | 1.35 | deliquescence |
| 12 | D-sorbitol[20] | 3.83 | deliquescence |
| 13 | trehalose[21] | 5.14 | n.d. |
| 14 | multitol[22] | 5.06 | n.d. |
| 15 | fructose[23] | 6.94 | n.d. |
| 16 | potato starch[24] | 7.52 | n.d. |
| 17 | rice starch[25] | 8.51 | n.d. |
| 18 | droxidopa alone (without disintegrant) | 2.73 | n.d. | n.d.: no data

From the above-mentioned results, it has been found that use of crystalline cellulose, D-mannitol, erythritol, glucose, sucrose, lactose, and corn-derived starch as additive enables production of a stable tablet with a low tendency toward coloring. In contrast, excipient Nos. 10-17 in Table 8 were found to show deliquescence and a tendency toward coloring.

Example 5

Droxidopa and the following excipients were mixed at 4:1 in a mortar and the mixture was compressed at a pressure of 20 kgf/cm² using an oil hydraulic press (manufactured by RIKEN). The obtained tablets were subjected to an experiment similar to that of Example 3.

TABLE 9

| No. | additive | 60° C. × 2 W color difference | 40° C. 75% × 2 W deliquescence |
|---|---|---|---|
| 1 | polyvinyl alcohol[26] | 3.27 | none |
| 2 | polyvinylpyrrolidone[27] | 4.63 | n.d. |
| 3 | hydroxypropylcellulose[28] | 9.67 | n.d. |
| 4 | hydroxypropyl methylcellulose[29] | 13.72 | n.d. |
| 5 | methylcellulose[9] | 17.83 | n.d. |
| 6 | droxidopa alone (without binder) | 2.73 | n.d. | n.d.: no data

From the above-mentioned results, it has been found that use of polyvinyl alcohol as a binder enables production of a stable tablet with a low tendency toward coloring. In contrast, binder Nos. 2-5 in Table 9 were found to show a high tendency toward coloring.

Example 6

Droxidopa starting drug having various average particle sizes described in the following Table 11 and the components of preparation 4 or 5 described in the following Table 10 were mixed and, using punch and die coated with magnesium stearate suspended in ethanol and dried, and an oil hydraulic table press (manufactured by NPa System Co., Ltd.), the mixture was compressed at a pressure of 1200 kgf to give tablets with diameter 10 mm, weight 400 mg.

TABLE 10

| formulation per tablet | preparation 4 (mg) | preparation 5 (mg) |
|---|---|---|
| L-threo DOPS | 200 | 200 |
| D-mannitol[1] | 180 | 176 |
| cornstarch[2] | 20 | 20 |
| citric anhydride[12] | 0 | 2 |
| aspartame[13] | 0 | 2 |
| St-Mg[3] | trace amount | trace amount |
| total | 400 | 400 |

All the prepared tablets disintegrated in the oral cavity in about 20-30 seconds. With 11 healthy test subjects, powderiness, and easy administrability were evaluated according to the evaluation criteria described in Tables 12 and 13. A method including disintegrating each tablet in the oral cavity, spitting out the tablet without swallowing and rinsing the mouth well with water was employed for the evaluation. The score values are the average values of all the test subjects.

The particle size and 90% D value of the starting drug were measured by a dry method using a Laser Diffraction Particle Size Analyzer (SHIMADZU SALD-3000J).

As for preparations 4 and 5, a mixture of components other than magnesium stearate (St-Mg) was charged in a spray granulator (RABO-1, manufactured by POWREX CORPORATION) or a flow coater (FLO-5, manufactured by Freund Corporation) and granulated while spraying 1% starch glue as a binding solution in an amount of 2.4 mg per tablet. As a binding solution, 1% dispersion was prepared by dispersing cornstarch in water and heating the dispersion until immediately before boiling. The inside of the fluidized bed was observed during granulation and producibility (easiness of production) was evaluated. After drying, the angle of repose of the granule was measured (angle of repose measurement device (manufactured by KONISHI SEISAKUSHO)).

better value as compared to one using the same starting drug and free of addition of flavor. As for the handling (producibility) during production, when the average particle size became ultrafine (10 μm or below), producibility was poor since attachment to the side surface of the inside of the fluidized bed was intense during granulation, and flowability of the granule tended to become poor. That is, the angle of repose was as high as 40 degrees or above, and the granule showed poor flowability.

The evaluation criteria of the powderiness and easy administrability in the above were as shown in the following Table 12 and Table 13.

(Evaluation Criteria of Powderiness)

TABLE 12

| Powderiness evaluation score | |
|---|---|
| not felt | 4 |
| does not bother | 3 |
| bothers somewhat | 2 |
| bothers | 1 |

Evaluation Criteria of Easy Administrability

TABLE 13

| easy administrability evaluation score | |
|---|---|
| can be administered with no problem | 4 |
| can be administered normally | 3 |
| can be administered with some effort | 2 |
| administration is difficult | 1 |

Table 14 shows the results of the stability test of preparations 4 and 5.

TABLE 14

| sample | evaluation | initial value | 60° C. × 2 W |
|---|---|---|---|
| preparation 4 (+silica gel) | judgment | – | ± |
| | color tone | white | pale-brown |
| | color difference (ΔE) | 0.00 | 1.53 |
| preparation 5 (+silica gel) | judgment | – | ± |
| | color tone | white | pale-brown |
| | color difference (ΔE) | 0.00 | 1.78 |

The produced preparations 4 and 5 were tightly sealed in a brown glass bottle in the presence of silica gel, preserved at

TABLE 11

| Preparation example | average particle size (μm) of starting drug | 90% D (μm) of starting drug | texture (powderiness) (score) | easy administrability (score) | handling during production (producibility) | angle of repose of granule |
|---|---|---|---|---|---|---|
| 4 | 48 | 154 | 2.5 | 2.9 | good | 39° |
| 4 | 39 | 138 | 2.7 | n.d. | good | 39° |
| 4 | 10 | 34 | 3.3 | n.d. | bad | 43° |
| 5 | 39 | 138 | 3.1 | 3.7 | n.d. | n.d. |
| 5 | 25 | 80 | n.d. | n.d. | good | 39° | n.d.: no data

The texture and easy administrability were better for smaller particle sizes. In addition, one added with a flavor using a small amount of organic acid and sweetener showed a 60° C. and changes in the appearance and analogous material were measured. As a result, the appearance changed little and 0.1% or more of an analogous material was not observed.

Example 7

Preparations 6 and 7 having formulations shown in the following Table 15 were produced. As for preparation 6, powder starting materials were mixed, and the mixture was tableted using the same method and conditions as in Example 6 to give tablets. As for preparation 7, starting materials were placed and mixed in a mortar, kneaded with a PVA binding solution at a concentration of 5%, dried at 80° C. for 1 hr, passed through a #30 sieve to give granules. Tabletting in the same manner as in preparation 6 gave tablets.

TABLE 15

| formulation per tablet | preparation 6 | preparation 7 |
|---|---|---|
| L-threo DOPS | 200 | 200 |
| D-mannitol[1] | 165 | 172 |
| cornstarch[2] | 19 | 20 |
| PVA[26] | 16 | 4 |
| St-Mg[3] | trace amount | trace amount |
| total | 400 | 396 |

Table 16 shows the results of the stability test of preparations 6 and 7.

TABLE 16

| sample | evaluation | initial value | 60° C. × 2 W |
|---|---|---|---|
| preparation 6 (+silica gel) | judgment | – | ± |
| | color tone | white | pale-brown |
| | color difference (ΔE) | 0.00 | 1.75 |
| preparation 7 (+silica gel) | judgment | – | ± |
| | color tone | white | pale-brown |
| | color difference (ΔE) | 0.00 | 1.68 |

The produced preparations 6 and 7 were tightly sealed in a brown glass bottle in the presence of silica gel, preserved at 60° C. and changes in the appearance and analogous material were measured. As a result, they were found to be preparations with small appearance change and small color difference.

INDUSTRIAL APPLICABILITY

According to the present invention, a droxidopa tablet superior in the handling property, stability and easy administrability can be provided without requiring a special preparation apparatus.

The invention claimed is:

1. A tablet consisting of
    (a) droxidopa as an active ingredient, wherein the content of droxidopa is 20-80 wt % relative to the total weight of the tablet,
    (b) at least one excipient selected from the group consisting of mannitol, lactose, erythritol, glucose, sucrose, and corn-derived starch,
    (c) a binder selected from the group consisting of corn-derived starch and/or polyvinyl alcohol,
    (d) optionally corn-derived starch as a disintegrant, and
    (e) optionally one or more additives selected from the group consisting of lubricants, sweeteners, acidulants, flavors, dyes, preservatives, antioxidants, stabilizers, and surfactants.
2. The tablet of claim 1, which is produced by a direct tabletting method.
3. The tablet of claim 1, wherein the binder is corn-derived processed starch.
4. The tablet of claim 3, wherein the corn-derived processed starch is partially or entirely pregelatinized cornstarch.
5. The tablet of claim 4, wherein the partially or entirely pregelatinized cornstarch is comprised in a proportion of 0.3-6% of the total weight.
6. The tablet of claim 1, wherein the binder is polyvinyl alcohol.
7. The tablet of claim 6, wherein the polyvinyl alcohol is comprised in a proportion of 0.001-5% of the total weight.
8. The tablet of claim 1, wherein the content of the excipient is 15-78 wt %.
9. The tablet of claim 1, which is produced via a granulation step using water.
10. The tablet of claim 1, which has a water content of 0.6 wt % or below relative to the total weight of the tablet.
11. The tablet of claim 1, which is rapidly disintegrated in the oral cavity and comprises the following (1), (2), and (3):
    (1) at least one excipient selected from the group consisting of mannitol, erythritol and lactose,
    (2) a disintegrant selected from the group consisting of cornstarch and/or partially pregelatinized corn-derived starch, and
    (3) a binder selected from the group consisting of corn-derived starch and/or polyvinyl alcohol.
12. The tablet of claim 11, wherein the binder is a partially or entirely pregelatinized cornstarch contained in a proportion of 0.5-3% of the total weight.
13. The tablet of claim 11, wherein the binder is polyvinyl alcohol contained in a proportion of 0.001-2% of the total weight.
14. The tablet of claim 11, wherein the weight ratio of excipient:total weight of corn-derived starch is 5:5-9.5:0.5.
15. The tablet of claim 11, wherein the excipient is mannitol.
16. The tablet of claim 1, wherein the droxidopa has an average particle size of 20 μm or above.
17. A method of preparing the tablet of claim 1, which method comprises:
    (1) granulating droxidopa,
    (2) drying a granulated production intermediate to give a granular production intermediate having a water content of 1 wt % or below, and
    (3) tabletting the granular production intermediate obtained in the aforementioned step (2) to provide the tablet.
18. The tablet of claim 5, wherein the content of the excipient is 15-78 wt %.
19. The tablet of claim 7, wherein the content of the excipient is 15-78 wt %.
20. The tablet of claim 5, which has a water content of 0.6 wt % or below relative to the total weight of the tablet.
21. The tablet of claim 7, which has a water content of 0.6 wt % or below relative to the total weight of the tablet.
22. The tablet of claim 5, wherein the droxidopa has an average particle size of 20 μm or above.
23. The tablet of claim 7, wherein the droxidopa has an average particle size of 20 μm or above.
24. A tablet consisting of
    (a) droxidopa as an active ingredient, wherein the content of droxidopa is 20-80 wt % relative to the total weight of the tablet,
    (b) at least one excipient selected from the group consisting of mannitol and corn-derived starch, wherein the content of the excipient is 15-78 wt % relative to the total weight of the tablet, (c) optionally corn-derived starch as a binder,
(d) optionally corn-derived starch as a disintegrant, and
(e) optionally one or more additives selected from the group consisting of lubricants, sweeteners, acidulants, flavors, dyes, preservatives, antioxidants, stabilizers, and surfactants.

25. The tablet of claim 24, wherein the content of droxidopa is not less than 40 wt % relative to the total weight of the tablet.

26. The tablet of claim 1, wherein the content of droxidopa is not less than 40 wt % relative to the total weight of the tablet.

27. The tablet of claim 1, wherein the excipient consists of mannitol and/or corn-derived starch.

28. A tablet which is rapidly disintegrated in the oral cavity consisting of
(a) droxidopa as an active ingredient, wherein the content of droxidopa is 20-80 wt % relative to the total weight of the tablet,
(b) at least one excipient selected from the group consisting of mannitol and corn-derived starch, wherein the content of the excipient is 15-78 wt % relative to the total weight of the tablet,
(c) a binder consisting of corn-derived starch,
(d) a disintegrant selected from the group consisting of cornstarch and/or partially pregelatinized corn-derived starch, and
(e) optionally one or more additives selected from the group consisting of lubricants, sweeteners, acidulants, flavors, dyes, preservatives, antioxidants, stabilizers, and surfactants.

29. The tablet of claim 28, wherein the content of droxidopa is not less than 40 wt % relative to the total weight of the tablet.

* * * * *